United States Patent
Hölzl et al.

(10) Patent No.: US 6,743,940 B2
(45) Date of Patent: Jun. 1, 2004

(54) 4-AMINOBUT-2-YNECARBOXYLIC ACID DERIVATIVES

(75) Inventors: Werner Hölzl, Eschentzwiller (FR); Wolfgang Haap, Grenzach-Wyhlen (DE); Jürgen Koppold, Lörrach (DE); Dietmar Ochs, Schopfheim (DE); Karin Petzold, Fischingen (DE); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 52 days.

(21) Appl. No.: 10/016,542

(22) Filed: Dec. 13, 2001

(65) Prior Publication Data
US 2002/0115881 A1 Aug. 22, 2002

(30) Foreign Application Priority Data
Dec. 15, 2000 (EP) .............................. 00811199

(51) Int. Cl.$^7$ ............................ C07C 229/00
(52) U.S. Cl. .................. 560/43; 560/155; 562/433; 562/553; 562/574
(58) Field of Search .................. 560/43, 155; 562/553, 562/574, 433

(56) References Cited

U.S. PATENT DOCUMENTS

| 4,684,661 A | 8/1987 | Stuetz | 514/443 |
| 6,002,008 A | 12/1999 | Wissner et al. | 546/160 |

FOREIGN PATENT DOCUMENTS

| EP | 0533352 | 3/1993 |
| WO | 94/29268 | 12/1994 |

OTHER PUBLICATIONS

Beart et al, Australian Journal of Chemistry, Acetylenic Analogues of gamma–Aminobutyric Acid, 1972, 25, pp. 1359–1361.*
Abulganieva et al, Izv. Minist. Nauki–Akad. Nauk Resp. Kaz., Ser. Khim., 1996, (1), pp. 81–87. English Abstract.*
Chemical Abstract vol. 128, No. 22, (1998), abstract No. 270425q for S.A. Viser et al., Izv. Minist. Nauki–Akad. Nauk Resp. Kaz., Ser. Khim., No. 5, (1997) pp. 46–52.
Chemical Abstract vol. 110, No. 13, (1989), abstract No. 114289w for Abdulganeeva et al., Zh. Org. Khim., vol. 24, No. 8, (1988), pp. 1772–1773.
Chemical Abstract vol. 108, (1988), No. 15, abstract No. 130721v for I. MacInnes et al., J. Chem. Soc., Perkin Trans. 2, No. 8 (1987), pp. 1077–1082.
Chemical Abstract vol. 98, (1983), No. 23, abstract No. 194315y for J. Diopoh et al., Bioorg. Chem., vol. 11, No. 4, (1982), pp. 463–477.
Derwent Abstract 67:64335 for J. Dumont et al., Bull. Soc. Chim. Fr. (1967), (4), pp. 1197–1203.
Chemical Abstract 127:108742 for S.A. Abdulganieva et al., Izv. Minist. Nauki–Akad. Nauk Resp. Kaz., Ser. Khim. (1996), (1), pp. 81–87.
Derwent Abstract 1995–234246 [47] for JP 07138230 (1995).
Chemical Abstract vol. 72, No. 17, (1970), abstract No. 89715 for A. Ceika et al., Liet. Tsr. Mokslu. Akad. Darb., Ser. B, No. 4, (1969), pp. 101–107.
Chemical Abstract vol. 55, No. 12, (1961), abstract No. 11294e for Ann. Chim., vol. 5, (1960), pp. 845–905.

* cited by examiner

Primary Examiner—Porfirio Nazario-Gonzalez
Assistant Examiner—Paul A. Zucker
(74) Attorney, Agent, or Firm—Kevin T. Mansfield

(57) ABSTRACT

There are described 4-aminobut-2-ynecarboxylic acid derivatives of formula

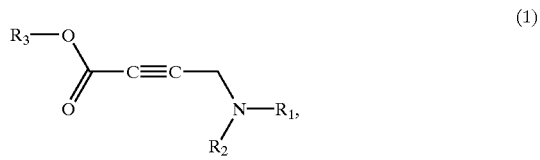

(1)

wherein $R_1$ and $R_2$ are each independently of the other hydrogen, $C_1$–$C_{20}$alkyl; $C_3$–$C_{12}$cycloalkyl; unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, naphthyl and naphthyl-$C_1$–$C_5$alkyl; and $R_3$ is $C_1$–$C_{20}$alkyl; $C_3$–$C_{12}$cycloalkyl.

The compounds exhibit a pronounced activity against gram-positive and gram-negative bacteria, and also against yeasts and moulds.

6 Claims, No Drawings

4-AMINOBUT-2-YNECARBOXYLIC ACID DERIVATIVES

The present invention relates to selected 4-aminobut-2-ynecarboxylic acid derivatives, to the preparation of such compounds, to the use of such compounds in the antimicrobial treatment of surfaces, as antimicrobial active ingredients against gram-positive and gram-negative bacteria, yeasts and fungi and in preserving cosmetics, household products, textiles, plastics and for use in disinfectants.

The compounds according to the invention correspond to the formula

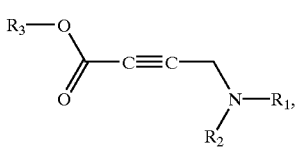

(1)

wherein
$R_1$ and $R_2$ are each independently of the other hydrogen, $C_1$–$C_{20}$alkyl; $C_3$–$C_{12}$cycloalkyl; unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, naphthyl or naphthyl-$C_1$–$C_5$alkyl, $R_3$ is hydrogen; $C_1$–$C_{20}$alkyl; or $C_3$–$C_{12}$cycloalkyl; there not being included compounds of formula (1) wherein
a) $R_1$ and $R_2$ are each independently of the other $C_1$–$C_3$alkyl; and
   $R_3$ is hydrogen; and
b) $R_1$ is methyl;
   $R_2$ is phenyl; or chloro-substituted phenyl; and
   $R_3$ is hydrogen, methyl or ethyl.

The invention preferably relates to compounds of formula (1) wherein
$R_1$ and $R_2$ are each independently of the other hydrogen; $C_1$–$C_{20}$alkyl; $C_1$–$C_5$alkoxy; unsubstituted or $C_1$–$C_5$alkyl- or halo-substituted phenyl or phenyl-$C_1$–$C_5$alkyl; and
$R_3$ is hydrogen; or $C_1$–$C_5$alkyl;
and especially to compounds of formula (1) wherein
$R_1$ and $R_2$ are each independently of the other hydrogen; $C_1$–$C_{20}$alkyl; $C_1$–$C_5$alkoxy; unsubstituted or $C_1$–$C_5$alkyl- or halo-substituted phenyl; and
$R_3$ is hydrogen; or $C_1$–$C_5$alkyl.

Special preference is given to compounds of formula (1) wherein
$R_1$ is $C_2$–$C_{20}$alkyl; $C_3$–$C_{12}$cycloalkyl; unsubstituted or $C_1$–$C_5$alkyl-, $C_3$–$C_{12}$cycloalkyl-, $C_1$–$C_5$-alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, naphthyl or naphthyl-$C_1$–$C_5$alkyl;

$R_2$ is unsubstituted or $C_1$–$C_5$alkyl-, $C_3$–$C_{12}$cycloalkyl-, $C_1$–$C_5$alkoxy-, $C_3$–$C_{12}$cycloakloxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, naphthyl or naphthyl-$C_1$–$C_5$alkyl; and $R_3$ is hydrogen; $C_1$–$C_{20}$alkyl; or $C_3$–$C_{12}$cycloalkyl.

Special preference is given to compounds of formula (1) wherein
$R_1$ is $C_2$–$C_{20}$alkyl; and
$R_2$ is unsubstituted or $C_1$–$C_5$alkyl-, $C_1$–$C_5$alkoxy-, halo-, trifluoromethyl- or pentafluoroethyl-substitute phenyl,
and especially to compounds of formula (1) wherein
$R_1$ and $R_2$ are each independently of the other hydrogen; or $C_4$–$C_{20}$alkyl.

Examples of especially preferred compounds according to the invention correspond to the formulae

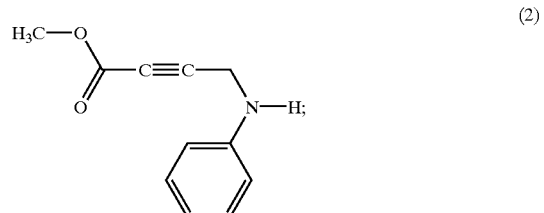

(2)

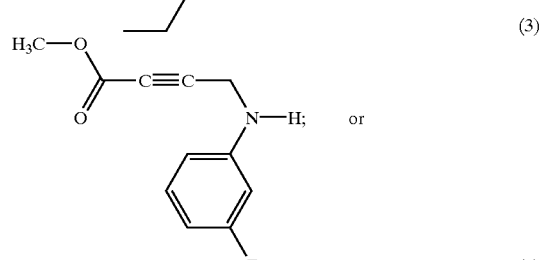

(3)

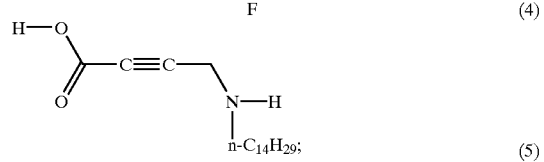

(4)

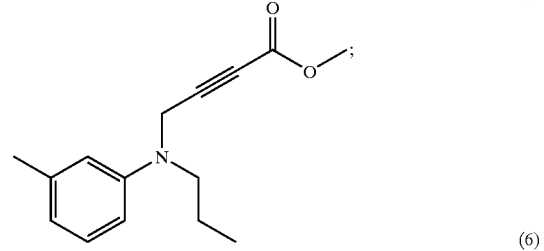

(5)

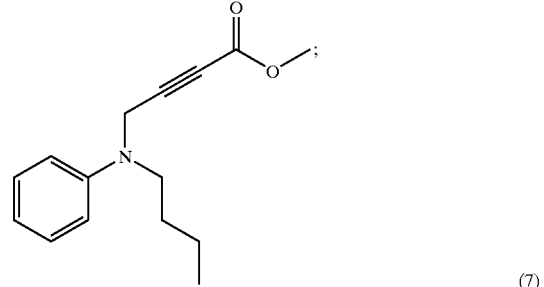

(6)

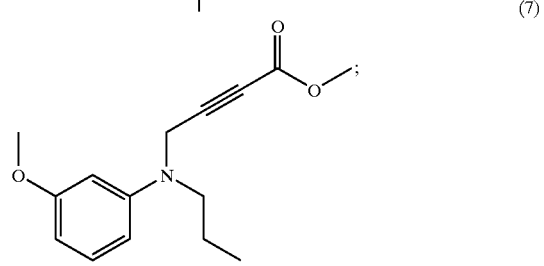

(7)

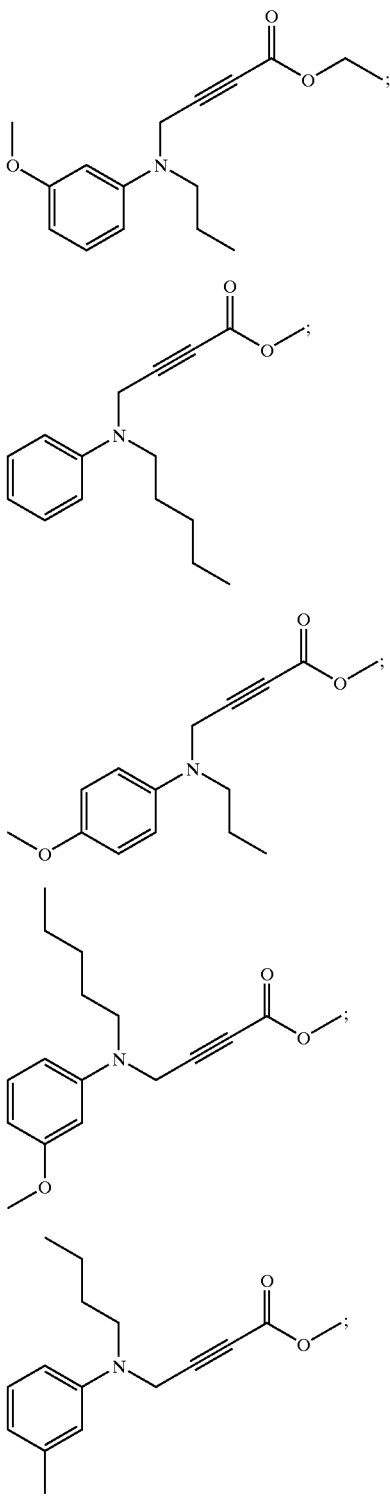

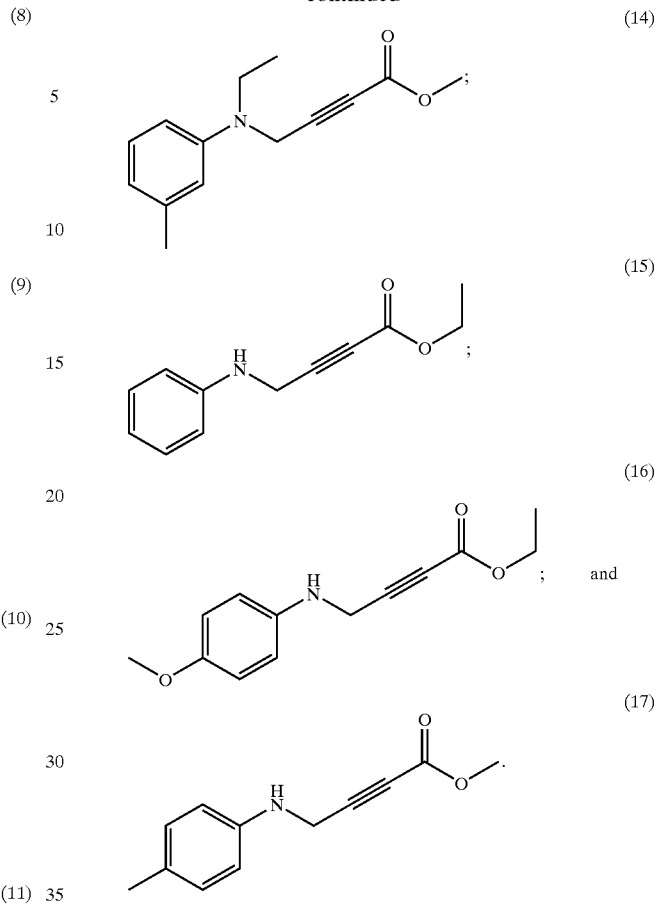

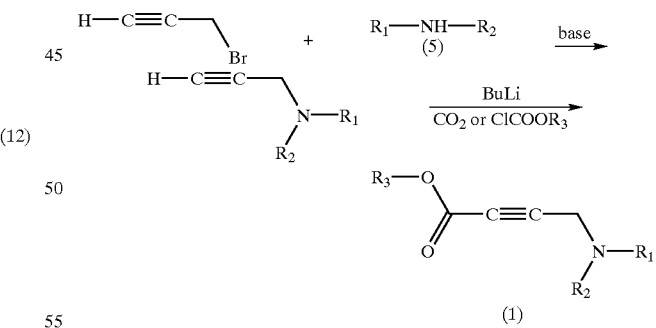

The 4-aminobut-2-ynecarboxylic acid derivatives according to the invention are prepared in a manner known per se by reacting an amine compound of formula (5) with propargyl bromide and, in a second reaction step, reacting the metallized acetylene with chloroformic acid esters or $CO_2$ in accordance with the following Reaction scheme:

In that Reaction scheme $R_1$ and $R_2$ are each independently of the other hydrogen, $C_1$–$C_{20}$alkyl; $C_3$–$C_{12}$cycloalkyl; unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, triflutrifluoromethyl-, pentafluoroethyl-, amino-, N,N-mono- or di-$C_1$–$C_{20}$alkylamino- or nitro-substituted phenyl or phenyl-$C_1$–$C_5$alkyl, naphthyl, naphthyl-$C_1$–$C_5$alkyl; and $R_3$ is hydrogen; $C_1$–$C_{20}$alkyl; or $C_3$–$C_{12}$cycloalkyl.

The invention relates also to the process for the preparation of the 4-aminobut-2-ynecarboxylic acid derivatives according to the invention.

The 4-aminobut-2-ynecarboxylic acid derivatives, according to the invention, of formula

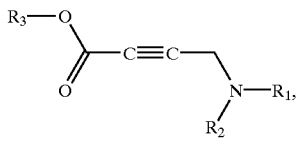

(1)

wherein $R_1$ and $R_2$ are each independently of the other hydrogen, $C_1$–$C_{20}$alkyl; $C_3$–$C_{12}$cycloalkyl; unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, naphthyl or naphthyl-$C_1$–$C_5$alkyl, $R_3$ is hydrogen; $C_1$–$C_{20}$alkyl; or $C_3$–$C_{12}$cycloalkyl; exhibit pronounced antimicrobial activity, especially against gram-positive and gram-negative bacteria and against bacteria of skin flora, and also against yeasts and moulds. They are accordingly suitable especially in the disinfection, deodorisation and general and antimicrobial treatment of the skin and mucosa and of integumentary appendages (hair), more especially in the disinfection of hands and of wounds.

They are therefore suitable as antimicrobial active ingredients and as preservatives in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation comprising at least one compound of formula (1) and cosmetically tolerable carriers or adjuvants.

The personal care preparation according to the invention comprises from 0.01 to 15% by weight, preferably from 0.1 to 10% by weight, based on the total weight of the composition, of the compound of formula (1) and cosmetically tolerable adjuvants.

Depending upon the form of the personal care preparation, it will comprise, in addition to the 4-aminobut-2-ynecarboxylic acid derivative of formula (1), further constituents, for example sequestering agents, colourings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of $C_{14}$–$C_{22}$fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion the cosmetically tolerable adjuvant preferably comprises from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. For example, the following preparations especially come into consideration:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipstick, lip gloss, lip contour pencils, nail-care preparations, such as nail varnish, nail varnish remover, nail hardeners, or cuticle removers;

intimate hygiene preparations, e.g. intimate washing lotions or intimate sprays;

foot-care preparations, e.g. foot baths, foot powders, foot creams or foot balsams, special deodorants and anti-perspirants or callous-removing preparations;

light-protective preparations, such as sun milks, lotions, creams, oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foam shaving creams, non-foaming shaving creams, foams, gels, pre-shave preparations for dry shaving, aftershaves or after-shave lotions;

fragrance preparations, e.g. fragrances (eau de Cologne, eau de toilette, eau de parfum, parfum de toilette, perfume), perfume oils or perfume creams;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hair sprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:
0.01 to 5% by weight of the compound of formula (1),
0.3 to 1% by weight titanium dioxide,
1 to 10% by weight stearic acid,
ad 100% soap base, e.g. the sodium salts of tallow fatty acid and coconut fatty acid or glycerols.

A shampoo has, for example, the following composition:
0.01 to 5% by weight of the compound of formula (1),
12.0% by weight sodium laureth-2-sulfate,
4.0% by weight cocamidopropyl betaine,
3.0% by weight NaCl and
water ad 100%.

A deodorant has, for example, the following composition:
0.01 to 5% by weight of the compound of formula (1),
60% by weight ethanol,
0.3% by weight perfume oil, and
water ad 100%.

The invention relates also to an oral composition, comprising
 0.01 to 15% by weight, based on the total weight of the composition, of the compound of formula (1) and orally tolerable adjuvants.
 Example of an oral composition:
10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The 4-aminobut-2-ynecarboxylic acid derivatives of formula (1) according to the invention are also suitable for the treatment, especially preservation, of textile fibre materials. Such materials are undyed and dyed or printed fibre materials, e.g. of silk, wool, polyamide or polyurethanes, and especially cellulose-containing fibre materials of all kinds. Such fibre materials are, for example, natural cellulose fibres, such as cotton, linen, jute and hemp, as well as cellulose and regenerated cellulose. Preferred suitable textile fibre materials are made of cotton.

The 4-aminobut-2-ynecarboxylic acid derivatives according to the invention are also suitable for the treatment of plastics, especially for imparting antimicrobial properties to or preserving plastics, e.g. polyethylene, polypropylene, polyurethane, polyester, polyamide, polycarbonate, latex, etc. Fields of use therefor are, for example, floor coverings, plastics coatings, plastics container and packaging materials; kitchen and bathroom utensils (e.g. brushes, shower curtains; sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the 4-aminobut-2-ynecarboxylic acid derivatives according to the invention.

It is also possible for nonwovens, e.g. nappies/diapers, sanitary towels, panty liners, and cloths for hygiene and household uses, to be provided with antimicrobial properties in accordance with the invention.

The 4-aminobut-2-ynecarboxylic acid derivatives of formula (1) are also used in washing and cleaning formulations, e.g. in liquid and powder detergents or fabric conditioners.

The 4-aminobut-2-ynecarboxylic acid derivatives of formula (1) can be used especially also in household and all-purpose cleaners for cleaning and disinfecting hard surfaces.

A cleaning preparation has, for example, the following composition:
0.01 to 5% of the compound of formula (1)
3.0% octyl alcohol 4EO
1.3% fatty alcohol $C_8$–$C_{10}$polyglucoside
3.0% isopropanol
ad 100% water.

In addition to preserving cosmetics and household products, it is also possible for technical products to be preserved and provided with antimicrobial properties; use as a biocide in technical processes is also possible, for example in paper treatment, especially in paper treatment liquors, printing thickeners of starch or cellulose derivatives, varnishes and paints.

The 4-aminobut-2-ynecarboxylic acid derivatives of formula (1) are also suitable for the antimicrobial treatment of wood and for the antimicrobial treatment of leather, the preservation of leather and the finishing of leather with antimicrobial properties.

The compounds according to the invention are also suitable for the protection of cosmetic products and household products from microbial damage.

The following Examples serve to illustrate the present invention but do not limit it.

EXAMPLE 1a

Preparation of N-methyl-N-phenyl-propargylamine
Reaction Scheme

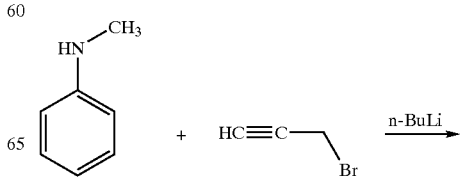

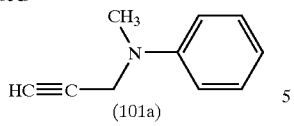

(101a)

34 ml of a 2.7M solution of n-butyllithium in n-heptane are added dropwise at room temperature under nitrogen in the course of 1 hour to a solution of 10 g (93 mmol) of N-methylaniline in 100 ml of absolute ether. The temperature increases to reflux of the reaction mass. After 1 hour's reflux, the yellow solution is cooled to −10° C. and then in the course of 30 minutes a solution of 11.3 g (102 mmol) of propargyl bromide in toluene is added dropwise. The mixture is then stirred at room temperature for 8 hours. After customary aqueous working-up, the product of formula (101a) is purified by distillation. A yellow oil is obtained. B.p. 45–50° C./$10^{-1}$ mbar, 4.2 g (31% of theory)

$^1$H-NMR (CDCl$_3$): 6.7–7.25 (m,5H, arom.-H), 3.95 (s,2H,NCH$_2$), 2.9 (s,3H,NCH$_3$), 2.1 (s, 1H,CH)

EXAMPLE 1b

Preparation of 4-(N-methyl-phenylamino)-but-2-yne-carboxylic Acid Methyl Ester Reaction Scheme

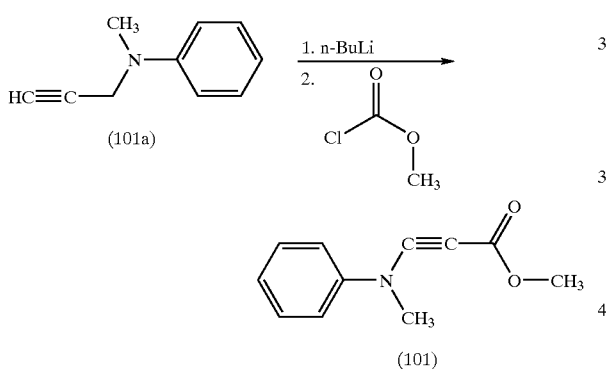

10.7 ml of a 2.7M solution of n-butyllithium in n-heptane are added dropwise at −78° C. to a solution of 4.2 g (29 mmol) of the amine of formula (101a) in 90 ml of absolute diethyl ether, and the mixture is stirred at that temperature for 1 hour. 3.8 g (40 mmol) of chloroformic acid methyl ester are then added dropwise. After 8 hours' stirring at −78° C. and heating to room temperature, customary aqueous working-up is carried out. The product is purified by distillation.

B.p. 120–125° C./$10^{-1}$ mbar, 3.1 g (16% of theory)

$^1$H-NMR (CDCl$_3$): 6.6–7.15 (m,5H, arom.-H), 4.0 (s,2H, NCH$_2$), 3.55 (s,3H,OCH$_3$), 2.8 (s,3H,NCH$_3$)

EXAMPLE 2

Preparation of 4-(N-methyl-phenylamino)-but-2-yne-carboxylic Acid Reaction Scheme

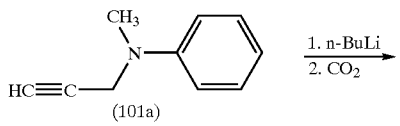

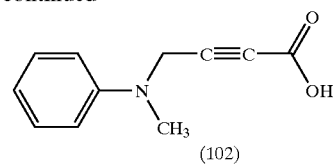

(102)

5 ml of a 2.7M solution of n-butyllithium in heptane are added at −10° C. to a solution of 2.1 g (15 mmol) of the amine of formula (101a) in 90 ml of diethyl ether, and then dry CO$_2$ gas is introduced until exothermic reaction is no longer detectable. After heating to room temperature, customary aqueous working-up is carried out and the product is obtained by extraction from a dilute hydrochloric emulsion in a purity of >90% in the form of a dark oil.

Yield: 1.0 g (11% of theory)

$^1$H-NMR (CDCl$_3$): 10.0 (s,1H,COOH), 6.8–7.25 (m,5H, arom.-H), 4.1 (s,2H,NCH$_2$), 2.9 (s,3H,NCH$_3$)

EXAMPLES 3 AND 4

General Preparation of Arylpropargylamines Reaction Scheme

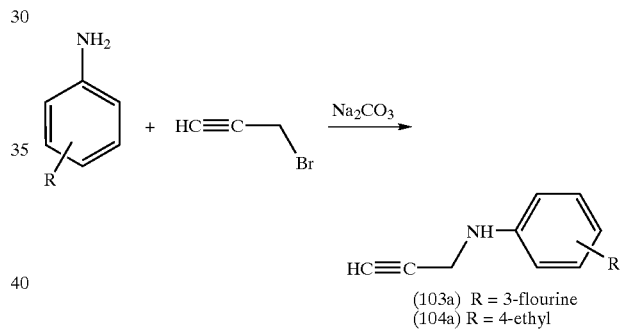

(103a) R = 3-flourine
(104a) R = 4-ethyl 13.1 g (125 mmol) of anhydrous sodium carbonate are added to a solution of 115 mmol of the amine in 100 ml of ethanol. After the dropwise addition of a solution of 14.9 g (125 mmol) of propargyl bromide in toluene at room temperature, heating at reflux is carried out, with vigorous stirring, for 12 hours. After cooling to room temperature, filtration and removal of the solvent, the residue is subjected to fractional distillation, yielding colourless oils:

|  | Yield [% of theory] | Bp/$10^{-2}$ mbar [° C.] | $^1$H-NMR (CDCl$_3$) [ppm] |
|---|---|---|---|
| (103a) | 64 | 60–63° C. | 6.4–7.2 (m,4H,arom.-H), 4.0(S$_{broad}$, 1H, NH), 3.9(s, 2H, NCH$_2$), 2.3(s, 1H, CH) |
| (104a) | 24 | 60–65° C. | 6.55–7.0(dd, 4H, arom.-H), 3.85(d, 2H, NCH$_2$), 3.7(s, 1H, NH), 2.5(q, 2H, C$\underline{H}_2$CH$_3$), 2.15(t, 1H, CH), 1.15(t, 3H, CH$_2$C$\underline{H}_3$) |

EXAMPLE 5

General Preparation of 4-(arylamino)-but-2-yne-carboxylic Acids Reaction Scheme

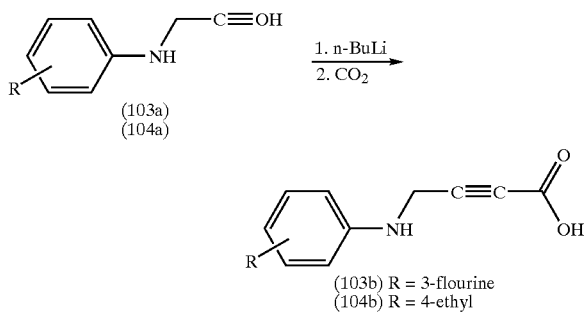

(103b) R = 3-flourine
(104b) R = 4-ethyl 3.5 ml of a 2.7M solution of n-butyllithium in n-heptane are added at −78° C. to a solution of 8.6 mmol of the arylpropargylamine of formula (103a) or (104a) in 20 ml of diethyl ether, and the mixture is stirred at that temperature for 1 hour. The reaction mass is then poured onto dry ice, heated at room temperature overnight and then subjected to customary aqueous working-up. The carboxylic acids are obtained in the form of colourless solids having a purity of >90%:

|  | Yield [% of theory] | $^1$H-NMR (DMSO-$d_6$) [ppm] |
|---|---|---|
| (103b) | 62 | 13.5(s, 1H, COOH), 6.4–7.2(m, 5H, arom.-H, NH), 4.15(s, 2H, NCH$_2$) |
| (104b) | 63 | 13.0(s, 1H, COOH), 6.6–7.05(dd, 4H, arom.-H), 5.95(S$_{broad}$, 1H, NH), 4.1(s, 2H, NCH$_2$), 2.45(q, 2H, C$\underline{H}_2$CH$_3$) 1.15(t, 3H, CH$_2$C$\underline{H}_3$) |

EXAMPLE 6

General Preparation of 4-(arylamino)-but-2-yne-carboxylic Acid Esters Reaction Scheme

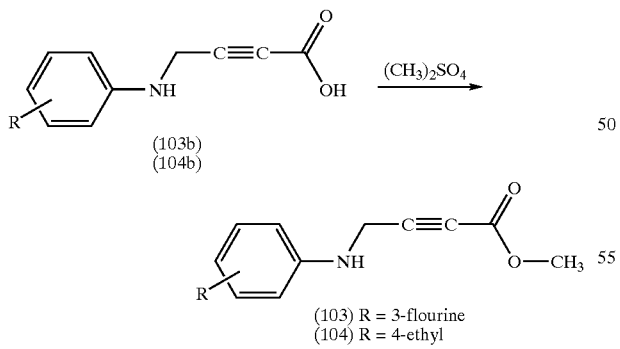

(103) R = 3-flourine
(104) R = 4-ethyl 0.6 g (4.4 mmol) of anhydrous K$_2$CO$_3$ and 0.8 ml (4.4 mmol) of dimethyl sulfate are added at room temperature to a solution of 3.9 mmol of the carboxylic acid of formula (103b) or (104b) in 20 ml of absolute acetone, and the mixture is then heated at reflux for 3 hours. After filtration, removal of the solvent and aqueous working-up, the esters are obtained in a purity of >90% in the form of yellow oils:

|  | Yield [% of theory] | m/z (GC/MS) | $^1$H-NMR (DMSO-$d_6$) [ppm] |
|---|---|---|---|
| (103) | 75 | 207 | 6.45–7.25(m, 5H, arom.-H, NH), 4.2(d, 2H, NCH$_2$), 3.75(s, 3H, OCH$_3$) |
| (104) | 72 | 217 | 6.5–6.95(dd, 4H, arom.-H), 5.85(t, 1H, NH), 4.05(d, 2H, NCH$_2$), 3.65(s, 3H, OCH$_3$), 2.4(q, 2H, C$\underline{H}_2$CH$_3$), 1.05(t, 3H, CH$_2$C$\underline{H}_3$) |

EXAMPLE 7

Preparation of Propargyl-n-tetradecylamine Reaction Scheme

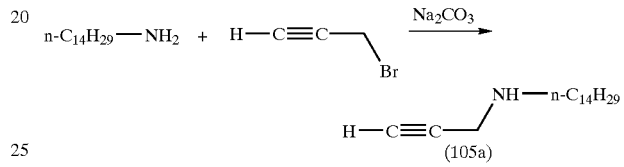

5 g (47 mmol) of anhydrous sodium carbonate are added to a solution of 10.0 g (47 mmol) of n-tetradecylamine in 100 ml of absolute acetone, and the suspension is heated to reflux. At that temperature 5.9 g (50 mmol) of propargyl bromide in 50 ml of acetone are then added dropwise and the mixture is subsequently heated at reflux for 2 hours. After aqueous working-up, the product is obtained in the form of a brown oil having a purity of >90%.

Yield: 8.2 g (70% of theory)

m/z=251 (GC/MS)

EXAMPLE 8

Preparation of 4-n-tetradecylamino-but-2-yne-carboxylic Acid

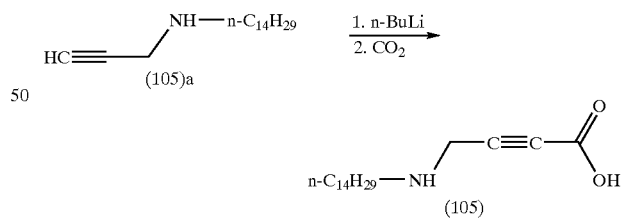

14 ml of a 2.7M solution of n-butyllithium in n-heptane are added dropwise at 25–30° C. to a solution of 8.2 g (33 mmol) of the amine of formula (105a) in 100 ml of absolute diethyl ether, and the mixture is then stirred for a further 3 hours. CO$_2$ gas is then introduced at room temperature until exothermic reaction is no longer observed. Aqueous working-up yields the compound of formula (105) in the form of a viscous brown mass having sufficient purity.

Yield: 1.5 g (11% of theory)

EXAMPLE 9

Determination of the Minimum Inhibitory Concentration (MIC) in the Agar Incorporation Test (MIC Test)

| | |
|---|---|
| Medium: | casein-soybean flour-peptone agar (Merck) |
| | *Sabouraud 4% glucose-agar (Merck) |
| Diluent medium: | sterile 0.85% NaCl solution |
| Test organisms: | *Staphylococcus aureus* ATCC 9144 |
| | *Escherichia coli* NCTC 8196 |
| | *Pseudomonas aeruginosa* CIP A-22 |
| | *Candida albicans* ATCC 10231 |
| | **Aspergillus niger* ATCC 6275 |
| Incubation: | 24 hours at 37° C. |
| | *3 days at 28° C. |
| Test solution: | 1% stock solutions of all the test substances are prepared in a suitable solvent and diluted in dilution series to end concentrations of from 1000 ppm to 10 ppm. |

Test Principle 0.3 ml of each dilution step is mixed with 15 ml of still liquid nutrient medium. After the nutrient medium has solidified, 10 μl of each of the following organism dilutions of the test strains in 0.85% NaCl solution is dotted onto the agar medium:

| | |
|---|---|
| *Staphylococcus aureus* ATCC 9144 | 1:100 dilution |
| *Escherichia coli* NCTC 8196 | 1:1000 dilution |
| *Pseudomonas aeruginosa* CIP A-22 | 1:1000 dilution |
| *Candida albicans* ATCC 10231 | 1:10 dilution |
| *Aspergillus niger* ATCC 6275 | 1:10 dilution |

The plates are incubated for 24 hours at 37° C. (*A. niger* 3 days at 28° C.) and then the highest dilution (lowest concentration) of the test substance at which no more growth is observed (corresponds to the MIC) is determined.

The results are shown in Table 1.

TABLE 1

| Compound of formula | (104) | (103) | (101) |
|---|---|---|---|
| *Staphylococcus aureus* ATCC 9144 | 250 | 500 | 62.5 |
| *Escherichia coli* NCTC 8196 | 250 | 500 | 125 |
| *Pseudomonas aeruginosa* CIP A-22 | 0 | 1000 | >1000 |
| *Candida albicans* ATCC 10231 | 125 | 250 | 62.5 |
| *Aspergillus niger* ATCC 6275 | 125 | 125 | 62.5 |

TABLE 2

Further microbiological test results

| Compound of formula | Structure | *Staphylococcus aureus* ATCC 9144 | *Aspergillus niger* ATCC 6275 |
|---|---|---|---|
| (106) | 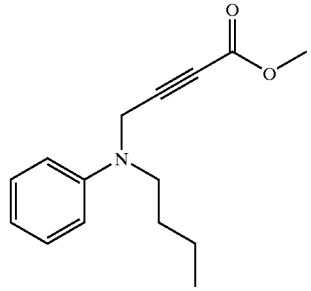 | 125 | 125 |
| (107) | 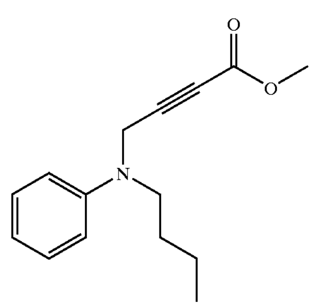 | 63 | 63 |

TABLE 2-continued

Further microbiological test results

| Compound of formula | Structure | *Staphylococcus aureus* ATCC 9144 | *Aspergillus niger* ATCC 6275 |
|---|---|---|---|
| (108) | 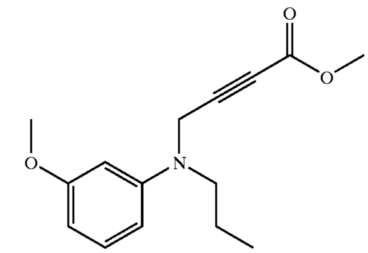 | 63 | 125 |
| (109) | 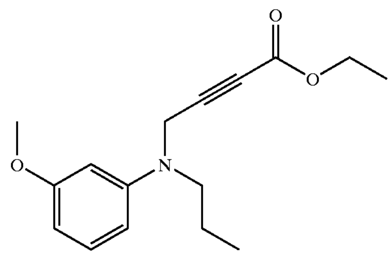 | 1000 | 0 |
| (110) | 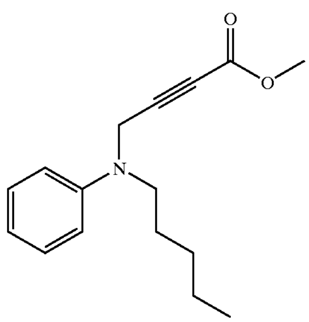 | 63 | 125 |
| (111) | 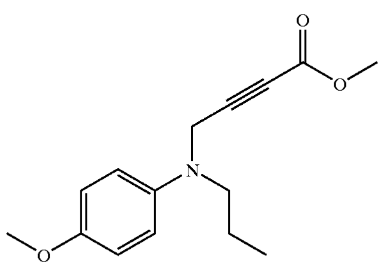 | 63 | 0 |
| (112) | 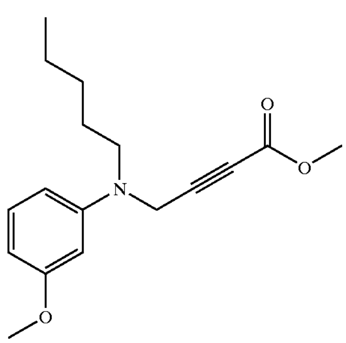 | 63 | 0 |

TABLE 2-continued

Further microbiological test results

| Compound of formula | Structure | *Staphylococcus aureus* ATCC 9144 | *Aspergillus niger* ATCC 6275 |
|---|---|---|---|
| (113) | 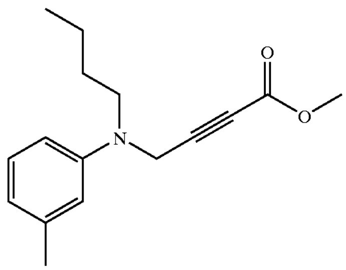 | 125 | 0 |
| (114) | 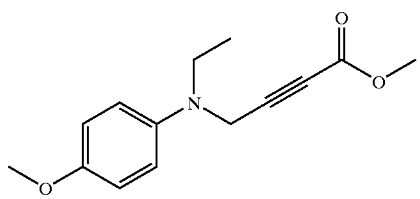 | 60 | 60 |
| (115) | 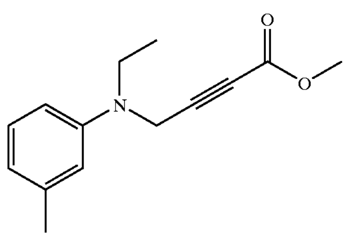 | 0 | 8 |
| (116) | 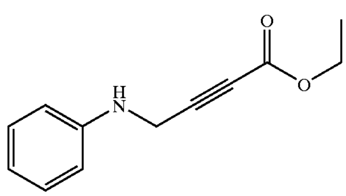 | 125 | 125 |
| (117) | 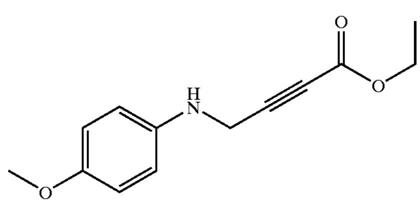 | 500 | 500 |
| (118) | 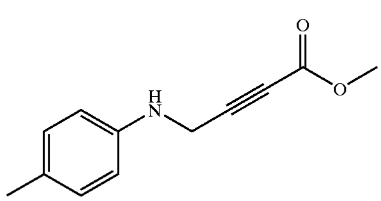 | 125 | 125 |

The results show a strong antimicrobial activity of the test substances against gram-positive and gram-negative bacteria and against fungi and yeasts.

What is claimed is:

1. A compound of formula

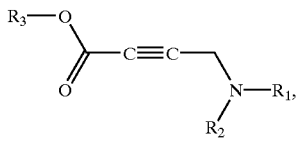

(1)

wherein

R$_1$ and R$_2$ are each independently of the other C$_1$–C$_{20}$alkyl; C$_3$–C$_{12}$cycloalkyl; unsubstituted or C$_1$–C$_5$alkyl-, C$_3$–C$_{12}$cycloalkyl-, C$_1$–C$_5$alkoxy-, C$_3$–C$_{12}$cycloalkoxy-, halo-, oxo-, carboxy-, carboxy-C$_1$–C$_7$alkyl ester-, carboxy-C$_3$–C$_{12}$cycloalkyl ester-, cyano-, trifluoromethyl-, pentafluoroethyl-, amino-, N,N-mono- or di-C$_1$–C$_{20}$alkylamino- or nitro- substituted phenyl, phenyl-C$_1$–C$_5$alkyl, naphthyl or naphthyl-C$_1$–C$_5$alkyl, R$_3$ is C$_1$–C$_{20}$alkyl; or C$_3$–C$_{12}$cycloalkyl;

there not being included compounds of formula (1) wherein
 a) R$_1$ and R$_2$ are each independently of the other C$_1$–C$_3$alkyl; and
 b) R$_1$ is methyl;

R$_2$ is phenyl; or chloro-substituted phenyl; and

R$_3$ is methyl or ethyl.

2. A compound according to claim 1 wherein

R$_1$ and R$_2$ are each independently of the other C$_1$–C$_{20}$alkyl; C$_1$–C$_5$alkoxy; unsubstituted or C$_1$–C$_5$alkyl- or halo-substituted phenyl or phenyl-C$_1$–C$_5$alkyl; and R$_3$ is C$_1$–C$_5$alkyl.

3. A compound according to claim 1 wherein

R$_1$ and R$_2$ are each independently of the other C$_1$–C$_{20}$alkyl; C$_1$–C$_5$alkoxy, unsubstituted or C$_1$–C$_5$alkyl- or halo-substituted phenyl; and R$_3$ is C$_1$–C$_5$alkyl.

4. A compound according to claim 1 wherein

R$_1$ is C$_2$–C$_{20}$alkyl; C$_3$–C$_{12}$cycloalkyl; unsubstituted or C$_1$–C$_5$alkyl-, C$_3$–C$_{12}$cycloalkyl-, C$_1$–C$_5$alkoxy-, C$_3$–C$_{12}$cycloalkoxy-, halo-, oxo-, carboxy-, carboxy-C$_1$–C$_7$alkyl ester-, carboxy-C$_3$–C$_{12}$cycloalkyl ester-, cyano-, trifluoromethyl-, pentafluoroethyl-, amino-, N,N-mono- or di-C$_1$–C$_{20}$alkylamino- or nitro-substituted phenyl, phenyl-C$_1$–C$_5$alkyl, naphthyl or naphthyl-C$_1$–C$_5$alkyl;

R$_2$ is unsubstituted or C$_1$–C$_5$alkyl-, C$_3$–C$_{12}$cycloalkyl-, C$_1$–C$_5$alkoxy-, C$_3$–C$_{12}$cycloalkoxy-, halo-, oxo-, carboxy-, carboxy-C$_1$–C$_7$alkyl ester-, carboxy-C$_3$–C$_{12}$cycloalkyl ester-, cyano-, trifluoromethyl-, pentafluoroethyl-, amino-, N,N-mono- or di-C$_1$–C$_{20}$alkylamino- or nitro- substituted phenyl, phenyl-C$_1$–C$_5$alkyl, naphthyl or naphthyl-C$_1$–C$_5$alkyl; and R$_3$ is C$_1$–C$_{20}$alkyl; or C$_3$–C$_{12}$cycloalkyl.

5. A compound according to claim 1, wherein

R$_1$ is C$_2$–C$_{20}$alkyl; and

R$_2$ is unsubstituted or C$_1$–C$_5$alkyl-, C$_1$–C$_5$alkoxy-, halo-, trifluoromethyl- or pentafluoroethyl-substituted phenyl.

6. A compound according to claim 1, wherein

R$_1$ and R$_2$ are each independently of the other C$_4$–C$_{20}$alkyl.

* * * * *